United States Patent

Soukup et al.

[11] Patent Number: 5,205,286
[45] Date of Patent: Apr. 27, 1993

[54] SUBCUTANEOUS ELECTRICAL DATA PORT

[75] Inventors: Thomas M. Soukup, Lake Jackson; Warren J. Block, Angleton, both of Tex.

[73] Assignee: Intermedics, Inc., Austin, Tex.

[21] Appl. No.: 734,947

[22] Filed: Jul. 24, 1991

[51] Int. Cl.$^5$ .......................... A61B 5/00; H01R 4/58
[52] U.S. Cl. .................... 128/630; 128/642; 128/899; 439/86
[58] Field of Search ................ 128/630, 899, 419 PS, 128/419 PT, 642, 784; 439/86

[56]         References Cited
        U.S. PATENT DOCUMENTS 4,712,557 12/1987 Harris .............................. 128/419 P
4,915,113  4/1990 Holman ............................... 128/691
4,941,472  7/1990 Moden et al. .................. 128/419 PS
5,131,854  7/1992 Jose et al. ............................ 439/86

Primary Examiner—Kyle L. Howell
Assistant Examiner—Kevin Pontius
Attorney, Agent, or Firm—John R. Merkling

[57]            ABSTRACT

A subcutaneous data port which may be surgically implanted beneath the skin of a subject and electrically connected to implanted leads, sensors or an implanted medica device. The data port provides electrical connections through conductive rubber access ports. The access ports can be penetrated by a coated needle, establishing an electrical connection. An indifferent plate electrode provides a replicable ground or body reference electrode.

5 Claims, 1 Drawing Sheet

SUBCUTANEOUS ELECTRICAL DATA PORT

FIELD OF OUR INVENTION

Our invention relates to implantable medical devices and in particular to apparatus for communicating data from within a living body to testing or recording equipment outside that body. Specifically we have invented a subcutaneous data port which permits temporary electrical connections to be made transcutaneously, connecting implanted sensors, medical devices, or other electrical apparatus with external electrical testing or recording apparatus.

BACKGROUND OF OUR INVENTION

The development of medical devices, drugs and treatments dependents on accurate data concerning the condition of a subject. For example, to develop a cardiac pacemaker or a implantable defibrillator, it is necessary to acquire information about the electrical functioning of the heart and about the response of the heart to stimuli of various kinds. This data may be acquired using animal test subjects. Although such testing is necessary, it should be conducted with a minimum of trauma and without multiple surgeries. Moreover, chronic exposure of leads or other connections through the skin should be avoided. It should be possible, from time to time, to make electrical connections with an implanted device so that accurate data can be acquired.

Similar considerations also apply to testing using implanted sensors or testing for the effects of drugs on the test subject.

It has been an object of our invention, therefore, to provide an apparatus which permits transcutaneous electrical connections to be made from time to time.

It has also been an object of our invention to provide such an apparatus which minimizes repetitive surgery, and which avoids chronic exposure of transcutaneous electrical connectors.

SUMMARY OF OUR INVENTION

We have invented a subcutaneous data port which may be surgically implanted beneath the skin of a subject and electrically connected to implanted leads, sensors or an implanted medica device. The data port provides electrical connections through conductive rubber access ports. The access ports can be penetrated by a coated needle, establishing an electrical connection. We have also provided an indifferent plate electrode which provides a replicable ground or body reference electrode.

DETAILED DESCRIPTION OF OUR PREFERRED EMBODIMENT

We will now describe our invention, referring to the accompanying drawings. Like numerals refer to like parts through out.

Figure 1:
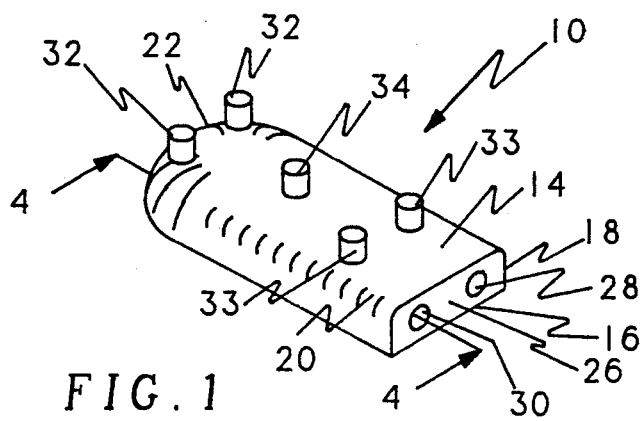
FIG. 1 is a perspective view of a subcutaneous data port according to our invention.
Figure 2:
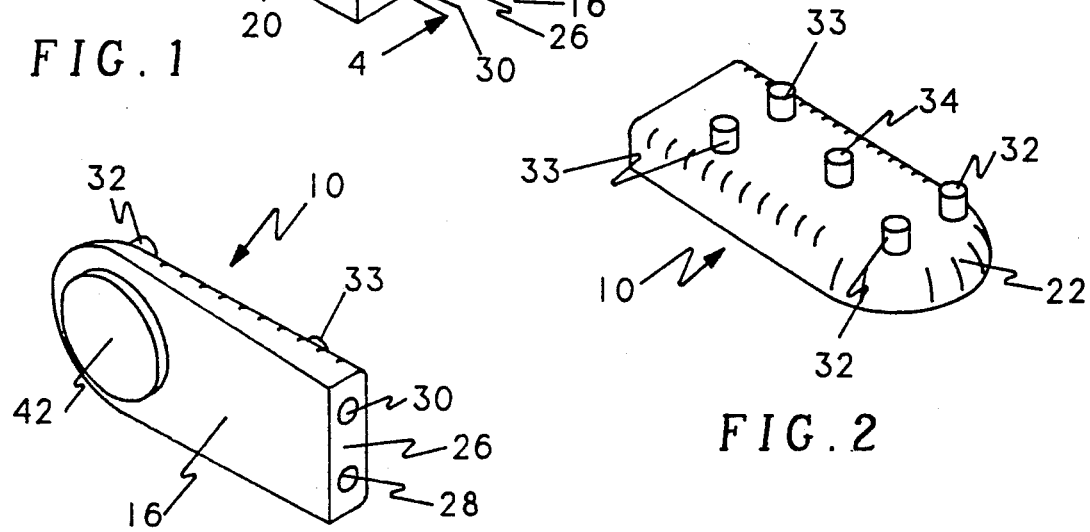
FIG. 2 is a reversed perspective view of the subcutaneous data port of FIG. 1.
Figure 3:
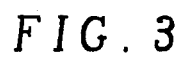
FIG. 3 is a bottom perspective view of the subcutaneous data port of FIG. 1.
Figure 4:
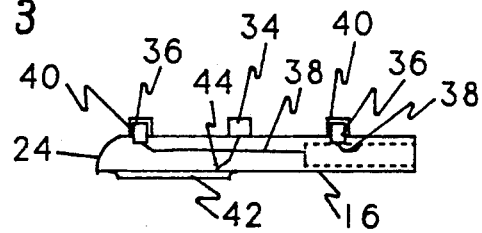
FIG. 4 is a through section of the subcutaneous data port taken along line 4—4 of FIG. 1.
Figure 5:
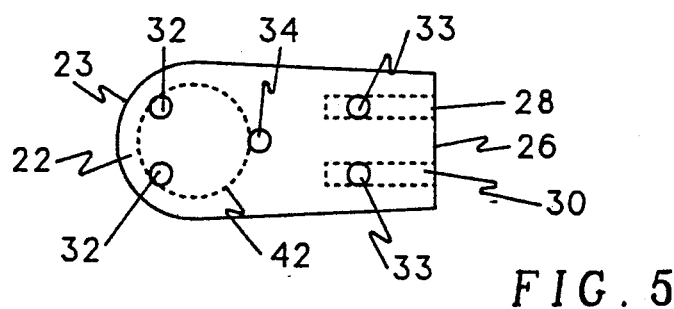
FIG. 5 is top view of the subcutaneous data port.

We have invented a subcutaneous data port, generally labeled 10, for providing temporary transcutaneous electrical connections in a living subject. The data port 10 comprises a non-conductive body 12. The body 12 is made of a biologically compatible material, preferably clear, non-conductive epoxy. In our preferred embodiment, the body 12 is generally flattened, to fit beneath the skin layer. An upper surface 14 will lie adjacent the underside of the skin surface while a lower surface 16 will lie against muscle or bone at an implant sight. Upper edges 18,20, adjacent the skin, are rounded. A distal end 22 is substantially semi-circular in outline 23 as seen in FIG. 5 and has a quarter section profile 24 as seen in FIG. 4. At a proximal end 26, connector ports, such as connector ports 28 and 30, are provided for making electrical connections with leads, implanted sensors or implanted medical devices, such as pacemakers. The connector ports 28,30 form electrical connections with male connectors and provide a seal against body fluids. This kind of electrical connection is known, particularly in the pacemaker art, and is analogous to the connection in a pacemaker header between the header and a pacemaker lead. The pacemaker industry has adopted a voluntary standard, a so-called SL-1 Standard Connector, and this is representative of our preferred embodiment.

On the upper side 14 of the body 12, a plurality of access ports are provided, such as distal access ports 32 and proximal access ports 33. In addition, a ground port 34 may also be provided. The access ports 32,33 and the ground port 34 are constructed in a similar fashion. The access ports comprise a conductive rubber filler 36 which is connected to a selected connector port 30 by a wire 38. We prefer the wire be a low resistance wire comprised of, for example, gold, silver DBS (drawn/brazed/stranded) or silver DFT (drawn/filament/tube) wire. The conductive filler 36 is covered by a silicone rubber cap 40. We prefer silicone rubber in the 40 to 80 durometer range. An indifferent plate 42 on the underside 16 of the body 12 provides a replicable ground or body reference electrode. When electrical measurements of body parameters are taken over a period of time, variation in measurement may be induced by change in a location of the ground or reference connection. An implanted, essentially permanent ground connection improves the accuracy of measured results. The indifferent plate 42 is connected to the ground port 34 by a low resistance wire 44.

In practice, the subcutaneous data prot is connected to leads, sensors or an implanted device through the connector ports and then positioned subcutaneously. The skin is closed, and allowed to heal. To establish an electrical connection, the investigator would locate the access ports by touch. In our preferred embodiment, the proximal access ports 33 are closer to the ground port 34 than are the distal access ports 32. This configuration permits the investigator to distinguish the ports and identify which port is associated with a particular implanted lead, sensor, or device. A conductive needle with a non-conductive sheath is inserted through the skin and into a selected access port. The needle penetrates the silicone rubber cap and enters the conductive rubber plug, establishing an electrical connection. The trauma associated with making an electrical connection is minimized, but a good electrical connection may be expected.

It will apparent to those skilled in the art that our invention may be embodied in other configurations without departing from the teachings or essential characteristics thereof. The foregoing description is, therefore, to be considered illustrative and not restrictive, and the scope of our invention is to be defined by the following claims. All changes or variations that would come within the meaning of equivalency of the claims are therefor intended to be incorporated therein.

We claim as our invention:

1. A subcutaneously implanted data port comprising a non-conductive body;
   at least one access sport on said body;
   said at least one access port comprising a conductive elastomeric filler and a non-conductive, penetrable cap, said cap covering said conductive elastomeric filler; and
   means for electrically connecting said data port to an implanted apparatus, said connecting means being in the electrical communication with said conductive elastomeric filler;
   an indifferent electrode on said body; and
   a ground port electrically connected to said indifferent electrode, said ground port comprising a conductive elastomeric ground filler and a non-conductive, penetrable ground cap, said ground cap covering said conductive ground filler.

2. The subcutaneously implantable data port according to claim 1 wherein said at least one access port comprises at least two access ports and said access ports and said ground port are arrange don said body in a pattern which permits the ports to be distinguished from one another.

3. The subcutaneously implantable data port according to claim 2 having four access ports disposed around said ground port, the ground port being centrally located on a side of said body adapted to be adjacent a skin layer, at least one of said access ports being closer to said ground port than at least one of the remaining access ports.

4. The subcutaneously implantable data port according to claim 3 wherein two of said access ports are a selected distance from said ground port and the remaining two of said access ports are a second selected distance from said ground port.

5. The subcutaneously implantable data port according to claim 4, said body comprising a semi-circular distal end spaced away from said connecting means.

* * * * *